United States Patent [19]

Yu et al.

[11] Patent Number: 6,004,529
[45] Date of Patent: Dec. 21, 1999

[54] CHELATING AGENTS

[75] Inventors: Shi-Bao Yu; Jasbir Singh, both of Wayne, Pa.

[73] Assignee: Nycomed Imaging AS, Oslo, Norway

[21] Appl. No.: 08/833,995

[22] Filed: Apr. 11, 1997

[51] Int. Cl.$^6$ .......................... A61K 51/04; A61K 5/055; C07D 213/04; C07C 319/00
[52] U.S. Cl. ................ 424/1.65; 424/1.65; 424/1.69; 424/9.34; 424/9.361; 424/9.4; 424/9.5; 424/9.6; 546/255; 546/256; 546/257; 568/57; 568/58; 568/61
[58] Field of Search ................... 424/1.65, 1.69, 424/9.3, 9.36, 9.364, 9.365, 9.4, 9.5, 9.6, 9.361, 9.34; 534/10, 14; 546/255, 256, 257; 568/57, 58, 61

[56] References Cited

U.S. PATENT DOCUMENTS

| 5,608,110 | 3/1997 | Ramalingam et al. | 564/253 |
|---|---|---|---|
| 5,632,969 | 5/1997 | Flanagan et al. | 424/1.69 |

FOREIGN PATENT DOCUMENTS

| 93 21957 | 11/1993 | WIPO . |
|---|---|---|
| 94 04485 | 3/1994 | WIPO . |
| 95 15769 | 6/1995 | WIPO . |
| 96 11918 | 4/1996 | WIPO . |

OTHER PUBLICATIONS

Mikako Fujita et al., J. Med. Chem., 39: 503–507 (1996).
Masami Otsuka et al., Bioorganic & Medicinal Chemistry, 5: 205–215 (1997).
Chiottellis E. et al., Nucl., Med. Biol. 15: 215–223 (1988).

*Primary Examiner*—Jose' G. Dees
*Assistant Examiner*—Michael G. Hartley
*Attorney, Agent, or Firm*—Bacon & Thomas

[57] ABSTRACT

The invention provides a complexant compound of formula I $$R^3S\,(CR^1{}_2)_nN(R^2)_i(CR^1{}_2)_nX(CR^1{}_2)_nN(R^2)_i(CR^1{}_2)_nSR^3 \qquad (I)$$

(wherein each n, which may be the same or different, is an integer 2, 3 or 4 (preferably 2); each i, which may be the same or different, represents 0 or 1; each $R^3$, which may be the same or different, is H or a thiol protecting group, preferably a protecting group; X is O, S, N, $NR^4$ or a substituted phosphorus (eg. oxo substituted phosphorus), preferably S or N; each $R^4$, which may be the same or different, is hydrogen or an optionally substituted organic group; each $R^1$, which may be the same or different, is hydrogen or an optionally substituted organic group, or a moiety $CR^1{}_2$ may represents a carbonyl group or two, three or four $R^1$s on two different carbons together with those carbons and any intervening atoms may represent an optionally substituted saturated or unsaturated homocyclic or heterocyclic ring; and preferably, at least one $CR^1{}_2$ moiety is other than $CH_2$ or $CH(CH_3)$) or a salt or complex thereof, wherein optionally at least one of the $R^1$, $R^2$, $R^3$ and $R^4$ moieties is coupled directly or indirectly to a vector moiety.

13 Claims, No Drawings

CHELATING AGENTS

This invention relates to complexants and metallated complexes thereof and to their use in diagnostic, therapeutic and prophylactic compositions, in particular to the use of such complexants metallated with radionuclides as diagnostic imaging and therapeutic agents.

Radiopharmaceuticals, the class of drug compounds containing radionuclides, are useful for the diagnosis and treatment of various disease states, in particular certain cancers. The radionuclide in such radiopharmaceuticals may be a metal (eg. a transition metal or lanthanide) or a non-metal (eg. an iodine or hydrogen radionuclide). Where the radionuclide is a metal, it is conventionally administered as a complex (usually a chelate complex) of a mono- or polyatomic ion of or containing the metal, with a complexing agent. The present invention is particularly concerned with complexed metal radionuclides and complexants which can be metallated with metal ion radionuclides.

In the use of complexed metal radiopharmaceuticals, the diagnostic or therapeutic properties are selected by appropriate selection of the metal radionuclide (eg. by virtue of its decay pattern or half life) while the biodistribution and bioelimination properties are selected by appropriate selection of the complexant and, if desired of a vector moiety coupled directly or indirectly to the complexant so as to cause the complexed radionuclide to be targeted to a particular body site or tissue type, eg. cancerous tissue.

Examples of complexants that have been proposed for use with metal radionuclides in therapeutic or diagnostic compositions include the terpyridine chelants disclosed in WO (TMT cases) and the BAT chelants discussed by Ohmomo et al. in J. Med. Chem. 35: 157–162 (1992) and by Kung et al. in J. Nucl. Med. 25: 326–332 (1984).

Nevertheless there is a continuing need for complexants which are capable of adequately complexing diagnostic and therapeutic metal radionuclides and which preferably also may be coupled to effective vector moieties so as to target the complexed radionuclide to a desired target site within the patient's body.

In particular there is a continuing need for complexants that may be used to complex both diagnostically effective metal radionuclides and therapeutically effective metal radionuclides. In this way a disease site may be imaged and treated using diagnostic and therapeutic agents which have substantially identical biodistributions since the carrier portion of the metal: carrier complex, which determines the biodistribution pattern of the complex, may be the same in both the diagnostic agent and the therapeutic agent.

We have now found that a new class of complexants possesses appropriate properties in this regard.

The novel complexants are referred to as $N_2S_2X$ complexants since they contain a carbon chain interrupted, in order by S, N, X, N and S heteroatoms (where X is an O, S, N or P heteroatom). Between these heteroatoms there are carbon chains 2, 3 or 4 atoms long. Such complexants, and the salts and complexes thereof, including the targeted complexes thereof, form one aspect of the invention. Viewed from a further aspect the invention provides a complexant compound of formula I

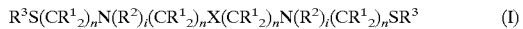

$$R^3S(CR^1{}_2)_nN(R^2)_i(CR^1{}_2)_nX(CR^1{}_2)_nN(R^2)_i(CR^1{}_2)_nSR^3 \quad (I)$$

(wherein each n, which may be the same or different, is an integer 2, 3 or 4 (preferably 2); each i, which may be the same or different, represents 0 or 1; each $R^3$, which may be the same or different, is H or a thiol protecting group, preferably a protecting group; X is O, S, N, $NR^4$ or a substituted phosphorus (eg. oxo substituted phosphorus), preferably S or N; each $R^4$, which may be the same or different, is hydrogen or an optionally substituted organic group; each $R^1$, which may be the same or different, is hydrogen or an optionally substituted organic group, or a moiety $CR^1{}_2$ may represents a carbonyl group or two, three or four $R^1$s on two different carbons together with those carbons and any intervening atoms may represent an optionally substituted saturated or unsaturated homocyclic or heterocyclic ring; and preferably, at least one $CR^1{}_2$ moiety is other than $CH_2$ or $CH(CH_3)$) or a salt or complex thereof, wherein optionally at least one of the $R^1$, $R^2$, $R^3$ and $R^4$ moieties is coupled directly or indirectly to a vector moiety.

Viewed from a further aspect the invention provides a pharmaceutical composition comprising an effective amount (eg. an amount effective to enhance image contrast in in vivo imaging or an amount sufficient to achieve a desired therapeutic effect) of a complex of an optionally vector coupled complexant of formula I together with at least one pharmaceutically effective carrier or excipient.

Viewed from a still further aspect the invention provides the use of a complex of an optionally vector coupled complexant of formula I for the manufacture of a contrast medium for use in a method of diagnosis involving administration of said contrast medium to an animate subject and generation of an image of at least part of said subject.

Viewed from a still further aspect the invention provides the use of a complex of an optionally vector coupled complexant of formula I for the manufacture of a therapeutic agent, eg a radiopharmaceutical, for example for use in tumor therapy.

Viewed from a still further aspect the invention provides a method of generating an image of an animate human or non-human (preferably mammalian or avian) animal subject involving administering a contrast agent to said subject, eg into the vascular system or the gi tract, and generating an image of at least a part of said subject to which said contrast agent has distributed, eg. by X-ray, MR, ultrasound, scintigraphic, PET, SPECT, electrical impedance, light or magnetometric imaging modalities, characterised in that as said contrast agent is used a complex of an optionally vector coupled complexant of formula I Viewed from a still further aspect the invention provides a method of treatment of an animate human or non-human (preferably mammalian or avian) animal subject involving administering a therapeutic agent to said subject, eg. into the vascular system or the gi tract, characterised in that as said therapeutic agent is used a complex of an optionally vector coupled complexant of formula I.

Viewed from a yet further aspect the invention provides a process for the preparation of a complex of an optionally vector coupled complexant of formula I, said process comprising metallating an optionally vector coupled complexant of formula I with a diagnostically or therapeutically effective metal ion or metal-containing complex ion.

Metallation may be effected using conventional techniques, eg. reacting the complexant or a salt thereof in solution with a soluble salt of the desired metal.

Where, in the compounds of formula I, $R^1$ groups together with intervening atoms form a cyclic group it is particularly preferred that this be a 5 to 8 membered ring containing 0, 1, 2 or 3 heteroatoms selected from N, S and O. More especially it is preferred that one such heteroatom is provided by a $N(R^2)_i$ or X group and it is even more especially preferred that the $R^1$ groups are on two carbons adjacent but on different sides of an $N(R^2)_i$ or X group. Preferably the compound of formula I will contain zero, one or three such heterocycles, preferably unsaturated and especially preferably aromatic heterocycles, incorporating ring nitrogens oxygens or sulphurs from $N(R^2)_i$ and X moieties. Particularly preferably the resultant heterocycle is an unsaturated $N_1$, $N_2$, $O_1$, $N_1O_1$ or $S_1$ heterocycle, preferably a thiophene, pyrrolidine, piperidine, piperazine, morpholine, pyran, pyrrole, imidazole, pyrazine, pyrimidine, imidazolidine, imidazolidinone, furan or pyridine ring. Pyridine, thiophen and furan rings, especially pyridine rings are especially preferred.

It is also preferred that the two $(CR^1_2)_n$ groups between the $N(R^2)_1$ and X moieties should be $(CH_2)_n$ or $(CR^1_2)(CH_2)_{n-1}$ groups where X is S and where the $CR^1_2$ moieties are attached to the $N(R^2)_i$ nitrogens. It is further preferred that the $(CR^1_2)$ groups adjacent a $(CR^1_2)$ group which is part of a cyclic group themselves should be part of a cyclic group or should be CH or $CH_2$ groups.

It is moreover preferred that the $CR^1_2$ moieties adjacent $SR^3$ groups should be $CH_2$ or $CR^5_2$ groups (where each $R^5$ is independently an alkyl group, preferably a $C_{1-3}$ alkyl group), especially preferably $CH_2$ or $C(CH_3)_2$ groups. Such $CR^1_2$ moieties are preferably $CR^5_2$ groups where the adjacent $(CR^1_2)_{n-1}N(R^2)_i$ group does not form part of a cyclic group.

Where a $CR^1_2$ group is a carbonyl group, this is preferably adjacent a $N(R^2)_i$ group. Where such a carbonyl group is present it is preferred that the other $CR^1_2$ group adjacent the $N(R^2)_i$ group should contain an amine or carbonyl function, eg. such a $CR^1_2$ group is a group CH—$CR_2COOH$ or CH—$CH_2CH_2NH_2$.

Any cyclic group formed by two $CR^1_2$ groups and intervening atoms may, as indicated above, be optionally substituted, eg. by at least one hydroxy, oxo, halo, alkyl, aryl, amino, CNS, carboxyl or acyl group, eg. by a hydroxy-amino-phenyl group.

Organic groups which are substituents on the compound of formula I will generally be $C_{1-20}$ groups, preferably $C_{1-10}$ groups, optionally containing one or more, eg. up to six heteroatoms (eg. halo, N, S, P and O atoms). Alkyl, alkenyl, alkynyl and acyl moieties (including alkylene etc. moieties) will preferably contain up to 6 carbon atoms- Aryl moieties will preferably be phenyl groups or 5 to 7 membered N, S or O heterocycles. However other hydrophilic substituents, such as polyalkylene oxides (ie. $((CH_2)_mO)_p$ where m is 2 or 3 and p is an integer of 2 to 500) may be present if desired as biodistribution modifiers.

Where two $NR^{12}$ groups are present, it is preferred that in at least one $R^2$ is an amine, carboxyl, or sulfur or phosphorus oxy-acid substituted $C_{1-6}$ alkyl group, eg. $CH_2CH_2NH_2$ or, more preferably, $CH_2COOH$.

Preferably the compounds of formula I are of formula II

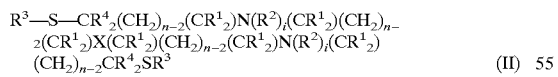
(II)

where each $CR^1_2$, which may be the same or different, is $CH_2$, CH or C, in the later cases being linked to a $CR^1_2$ group adjacent the same heteroatom to form an optionally substituted saturated or unsaturated 5 or 6-membered heterocycle, and each $R^2$ where present is H or a functionalized $C_{1-6}$ alkyl group (eg. $CH_2COOH$), preferably one $R^2$ being other than H.

Particularly preferably, each n is 2, X is S or N and O, 1 or 2 fused pyridine groups are present in the compounds of the invention. Thus, particularly preferred compounds include those of formulae III to

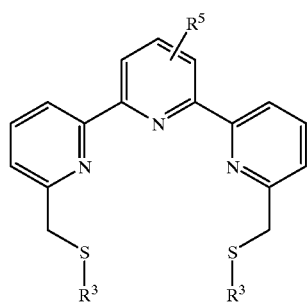
(III)

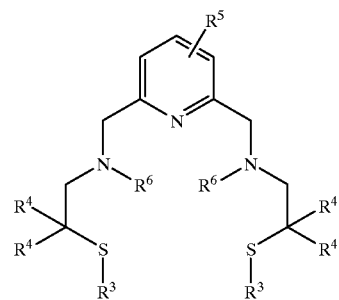
(IV)

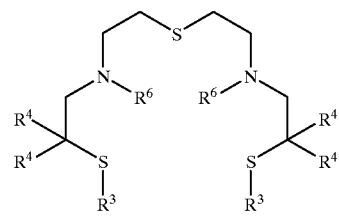
(V)

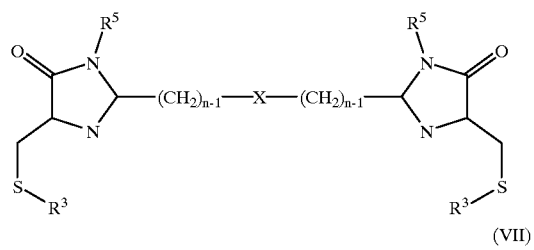
(VI)

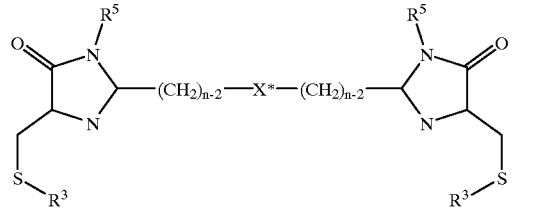
(VII)

(where $R^5$ is hydrogen or optionally substituted alkyl, aryl, alkaryl or aralkyl; $R^4$ is H or, preferably, $CH_3$; $R^6$ is H or functionalized alkyl, preferably one being H and the other being $CH_2COOH$; and $X^*$ is a carbon attached heteroaromatic ring, eg. a 2,5-thiophene, 2,6-pyridine, 2,5-furan or 2,6-pyrimidine ring, optionally substituted by a Rs group).

Direct linkage to a vector group is preferably via a backbone carbon of a $(CR^1_2)_n$ moiety or via a ring carbon of a cyclic group formed by two $(CR^1_2)$ groups and an intervening heteroatom of $N(R^1_2)_i$ or X, particularly preferably via a phenyl group attached to such a ring atom.

The thiol protecting group $R^3$ may be any of the known thiol protecting groups (see for example Greene, "Protective groups in organic synthesis", Wiley Interscience, 1981 and McOmie, "Protective groups in organic chemistry", Plenum, 1973). Examples of such groups include optionally substituted $C_{1-6}$ alkyl groups, eg. methoxy benzyl (mBz) groups.

The complexants of the invention may be coupled to a vector, a material which will affect the hiodistribution of the complexant or its complexes, eg. to target it to particular receptors, organs, tissues or body compartments. Such coupling may be direct or may involve a linker, a bifunctional compound which binds to the complexant and the vector. Examples of suitable vectors include proteins, antibodies, antibody fragments, oligopeptides, hormones, polyalkylene oxides, and pharmaceuticals. (See for example WO 92/08494).

The compounds of the invention may be prepared by routine organic synthesis and chelator metallation techniques. Illustrative synthetic schemes are shown below.

Scheme 1. Synthesis of TMT-S2

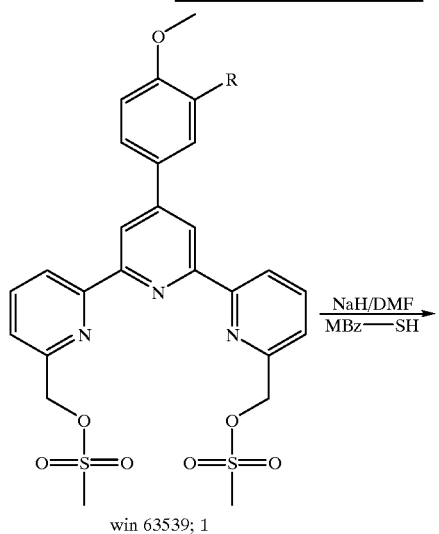

Scheme 2. Synthesis of precursors

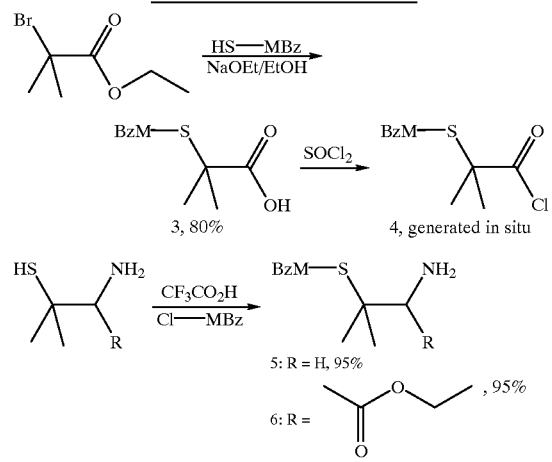

Scheme 3. Synthesis of N2S2-pyridine

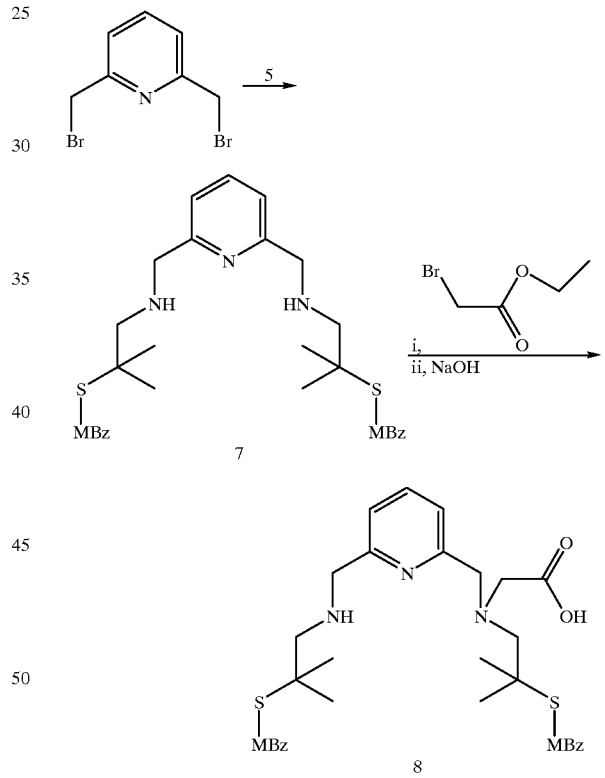

Scheme 4. Synthesis of N2S2X

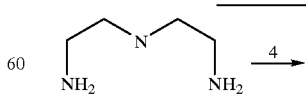

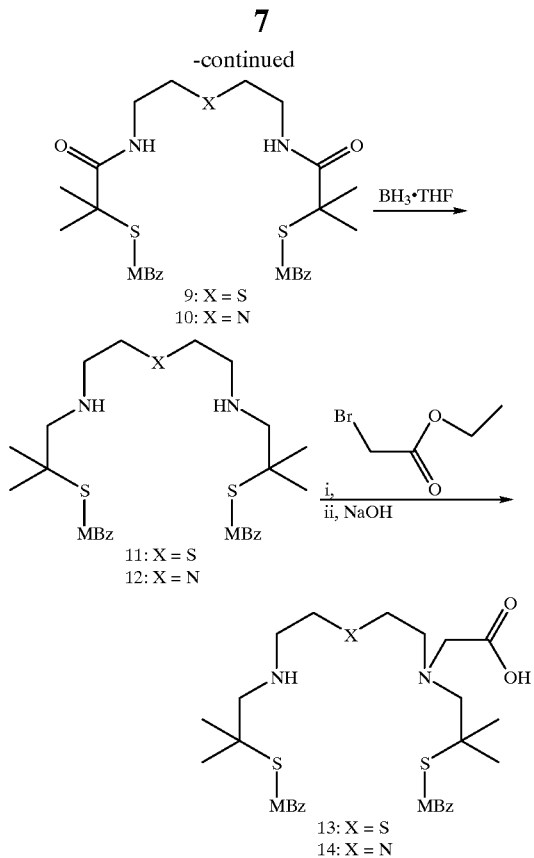

9: X = S
10: X = N

11: X = S
12: X = N

13: X = S
14: X = N

Scheme 5. Synthesis of N2S2X-amide

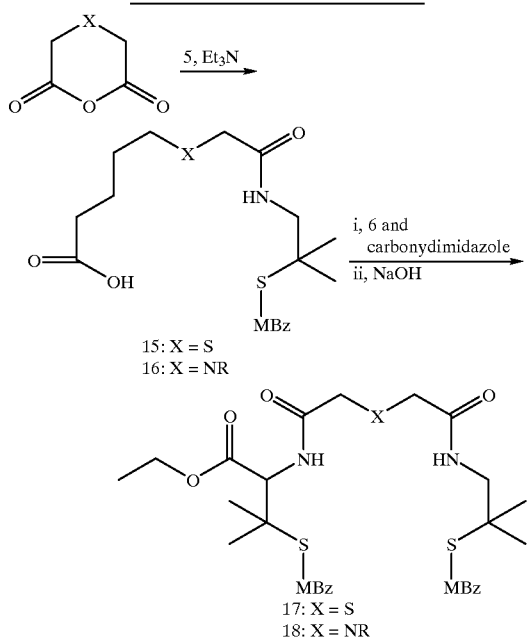

15: X = S
16: X = NR

17: X = S
18: X = NR

The complexant compounds of formula I may be metallated with therapeutically or diagnostically effective metal ions or complex ions (eg. metal oxide or metal sulphide ions (such as TcO or VO)). Generally speaking, preferred metal ions will be radionuclides, paramagnetic ions, fluorescent ions, or heavy metal ions (eg. with atomic number greater than 53) or cluster ions.

Examples of appropriate metals include Ag, At, Au, Bi, Cu, Ga, Ho, In, Lu, Pb, Pd, Pm, Pr, Rb, Re, Rh, Sc, Sr, Tc, Tl, Y, and Yb.

Preferred metal radionuclides include $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{100}$Re, $^{177}$Lu, $^{199}$Au, $^{47}$Sc, $^{67}$Ga, $^{51}$Cr, $^{177m}$Sn, $^{67}$Cu, $^{167}$Tm, $^{97}$Ru, $^{100}$Re, $^{177}$Lu, $^{199}$Au, $^{203}$Pb and $^{141}$Ce.

Moreover γ-emitting radionuclides, such as $^{99m}$Tc, $^{111}$In, $^{67}$Ga and $^{169}$Yb have been approved or under investigation for diagnostic imaging, while complexes of γ-emitters, such as $^{67}$Cu, $^{111}$Aq, $^{186}$Re and $^{90}$Y are most promising for the applications in tumor therapy. Also γ-emitters (examples are $^{99m}$Tc, $^{111}$In, $^{67}$Ga and $^{169}$Yb) but also to the β-emitters (such as $^{67}$Cu, $^{111}$Ag, $^{186}$Re, $^{188}$Re and $^{90}$Y), as well as other radionuclides of interest ($^{211}$At, $^{212}$Bi, $^{177}$Lu, $^{86}$Rb, $^{105}$Rh, $^{153}$Sm, $^{198}$Au, $^{149}$Pm, $^{85}$Sr, $^{142}$Pr, $^{214}$Pb, $^{109}$Pd, $^{166}$Ho, $^{208}$Tl, and $^{44}$Sc). Complexes with hard metal ions, such as In$^{3+}$, Ga$^{3+}$, Yb3+, and Y$^{3+}$, shall be stable In addition, since they contain two or three sulfur atoms, their soft metal (Ag$^+$, Cu$^{2+}$, TcO$^{3+}$, and ReO$^{3+}$) complexes should also be stable.

Preferred paramagnetic metal ions include ions of transition and lanthanide metals (eg. metals having atomic numbers of 21–29, 42, 43, 44, or 57–71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

Preferred fluorescent metal ions include lanthanides, in particular La, Ce, Pr, Nd, Pm, Sm, Eu, Gd, Tb, Dy, Ho, Er, Tm, Yb, and Lu. Eu is especially preferred.

Preferred heavy metal-containing reporters may include atoms of Mo, Bi, Si, and W, and in particular may be polyatomic cluster ions (eg. Bi compounds and W and Mo oxides) as described in WO91/14460, WO92/17215, WO96/40287, and WO96/22914.

All of the publications referred to herein are incorporated herein by reference.

The compounds of the invention may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight Where the chelated species is a radionuclide, dosages of 0–01 to 100 mCi, preferably 0.1 to 50 mCi will normally be sufficient per 70 kg bodyweight.

The dosage of the compounds of the invention for therapeutic use will depend upon the condition being treated, but in general will be of the order of from 1 pmol/kg to 1 mmol/kg bodyweight.

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc. However, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

For imaging of some portions of the body the most preferred mode for administering contrast agents is parenteral, egg., intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

The invention is illustrated further by the following non-limiting Examples. Compound numbering is as in the reaction schemes illustrated above

EXAMPLE 1

Preparation of 2: To a solution of 76 mg of NaH in 10 mL DMF under $N_2$, 0.27 mL of 4-methoxyl benzyl thiol was added while stirring. Then 0.48 g WIN 63539 solid was added, the mixture was stirred overnight. The mixture was diluted with $CHCl_3$, washed with $H_2O$, 10% $Na_2CO_3$ and brine, dried over $Na_2SO_4$. It was filtered and 2 was obtained as an off-white solid after the solvent was removed by rotary evaporation. The yield is 80% and 2 was characterized by TLC and NMR.

EXAMPLE 2

Preparation of 3 and 4: 3 was prepared through a known procedure by reaction of ethyl 2-bromo-2-methyl propionate with HS-MBz in sodium ethoxide/ethanol with yields between 60% to 80%. The crude product was used in the subsequent in situ generation of 4.

EXAMPLE 3

Preparation of 5: To a solution of 18.2 g of 1-Amino-2-methyl-2-propanethiol hydrochloride in 150 mL $CH_2Cl_2$ and 21 mL trifloroacetic acid at 0° C., a cold solution of 20.1 g 4-miethoxylbenzyl chloride in 50 mL $CH_2Cl_2$ was added dropwise. The mixture was stirred at 0° C. for 1 hr and in room temperature for 3 hr. MeOH 30 mL was added to the mixture to terminate the reaction and all solvents was removed by rotary evaporation. The residue was dissolved in 400 mL $CHCl_3$, washed with sat. $NaHCO_3$ 3×300 mL, 10% $Na_2CO_3$, $H_2O$, and brine, dried over $Na_2SO_4$. It was filtered and 5 was obtained as a colorless oil after the solvent was removed by rotary evaporation. The yield was 95% and 5 was characterized by TLC and NMR.

EXAMPLE 4

Preparation of 6: It was prepared by same procedure as that of 5 using L-Cysteine ethyl ester hydrochloride. The yield was 95% and 6 was characterized by TLC and NMR.

EXAMPLE 5

Preparation of 7: To a solution of 2,6-bis(bromomethyl) pyridine in MECH, diisopropyl ethylamine and 5 are added, the mixture is heated to reflux for 3 days and is allowed to cool to room temperature. Extraction techniques and silica chromtatography afford 7.

EXAMPLE 6

Preparation gf 8: To a solution of 7 in MeCN, diisopropyl ethylamine and ethyl bromoacetate are added, the mixture is heated to ref lux overnight and usual extraction techniques and silica chromatography afford 8.

EXAMPLE 7

Preparation of 9: To a solution of 3 (5 g) in $CHCl_3$, 6.6 MnL $SOCl_2$ was added dropwise, then the mixture was refluxed for 3 hr. Solvent was removed by rotary evaporation and 50 mL $CH_2Cl_2$ war added to the residue at 0° C. 3.4 mL $Et_3N$ was added slowly and then a solution of 1.1 g 2,2'-bisaminoethyl thioether in 10 mL $CH_2Cl_2$ was added dropwise. The mixture was allowed to warm to room temperature arid then was heated to ref lux for 3 hr. it was allowed to cool to room temperature and was transferred to a separation funnel, washed with sat. $NaHCO_3$, 10% $Na_2CO_3$, $H_2O$, 1N KCl, $H_2O$, and brine, dried over $Na_2SO_4$. It was filtered and the crude product was obtained after the solvent was removed by rotary evaporation. It was purified by silica chromatography (50%:50%/ethyl acetate:hexane) and 9 was obtained as a colorless oil. The yield was 50% and 9 was characterized by TLC and NMR.

EXAMPLE 8

Preparation of 10: It is prepared and isolated in a similar procedure as to that of 9, using diethylene triamine. Usual isolation and purification procedures afford a pure product.

EXAMPLE 9

Preparation of 11: To a solution of 5.3 g 9 in 40 mL of THF, 40 mL of 1 N $BH_3$•THF was added. The mixture was heated to reflux for 48 hr and was allowed to cool to room temperature. About 10 mL 6 N NaOH was added to Adecompose the excess $BH_3$ and the mixture was refluxed for 30 min. 2 N HCl was added to adjust pH to acidic, and all solvent was removed by rotary evaporation. The residue was dissolved in CHCl3, washed with $H_2O$, sat. $NaHCO_3$, $H_2O$, and brine, dried over $Na_2SO_4$. It was filtered and the crude product was purified by silica chromatography (90%:10%/ ethyl acetate:MeOR) and 11 was obtained as a colorless oil. The yield was ~50% and 11 was characterized by TLC and NMR.

EXAMPLE 10

Preparation of 12: It is prepared and isolated in a similar procedure as to that of 11, using 10 as the starting material. Usual isolation and purification procedures afford a pure product.

EXAMPLE 11

Preparation of 13: To a solution of 2.9 g 11 in 100 mL MeCN, 0.79 g diisopropylethyl amine and 0.94 g ethyl bromoacetate were added. The mixture was heated to reflux for 24 hr and was allowed to cool to room temperature. Solvent was removed by rotary evaporation and the residue wag dissolved in CHCl$_3$, washed with H$_2$O , sat. NaHCO$_3$, H$_2$O, and brine, dried over Na$_2$SO$_4$. It was filtered and the crude product was purified by silica chromatography (90%:10/ethyl acetate:hexane). It was dissolved in a mixture of 20 mL THF and 20 mL 5 N NaOH. The mixture was refluxed for 1 hr and was allowed to cool to room temperature. The pH of the solution was adjusted to ~10 with 1 N HCl and it was extracted with CH$_2$Cl$_2$. The organic phase was washed with H$_2$O, 10% Na$_2$CO$_3$, H$_2$O , and brine, dried over Na$_2$SO$_4$. It was filtered and 13 was obtained as a white solid. The final yield was ~40% and 13 was characterized by TLC and NMR.

EXAMPLE 12

Preparation of 14: It is prepared and isolated in a similar procedure as to that of 13, using 12 as the starting material. Usual isolation and purification procedures afford a pure product.

EXAMPLE 13

Preparation of 15: To a solution of 8.6 g 5 in 150 mL CH$_2$Cl$_2$ at 0° C., 5.3 g thioglycolic anhydride solid was added slowly and the mixture was stirred for 4 hr. It was transferred to a separation funnel, washed with H$_2$O, 10% Na$_2$CO$_3$, H$_2$O, and brine, dried over Na$_2$SO$_4$. It was filtered and 15 was obtained as a colorless oil after the solvent was removed by rotary evaporation. The yield was 90% and 15 was characterized by TLC and NMR.

EXAMPLE 14

Preparation of 16: It is prepared and isolated in a similar procedure as to that of 15, using amine-protected iminodiacetic anhydride as the starting material. Usual isolation and purification procedures afford a pure product.

EXAMPLE 15

Preparation of 17: To a solution of 6.5 g 15 in 150 mL CHCl$_3$, 4.4 g carbonyldiimidazole solid was added slowly and the mixture was stirred for 30 min. Then a solution of 5.7 g 6 in 50 mL, CHCl$_3$ was added and the mixture was stirred overnight. It was transferred to a separation funnel, washed with H$_2$O, 1N HCl, H$_2$O 10% Na$_2$CO$_3$, H$_2$O, and brine, dried over Na$_2$SO$_4$. It was filtered and the crude product was purified by silica chromatography (90%:10%/ethyl acetate:hexane). The yield was 60% and 17 was characterized by TLC and NMR.

EXAMPLE 16

Pceproation of 18: It is prepared and isolated in a similar procedure as to that of 17, using 16 as the starting material Usual isolation and purification procedures afford a pure product.

We claim:
1. A complexant compound of formula III

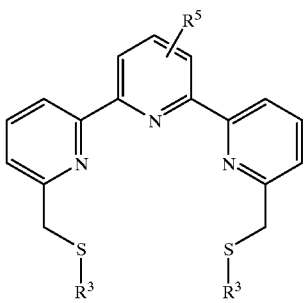

(III)

wherein each R$^3$, which may be the same or different, is H or a thiol protecting group; and R$^5$ is hydrogen or optionally substituted alkyl, aryl, alkary or aralkyl, or a salt or complex thereof.

2. A compound of claim 1 which is metallated with at least one therapeutically or diagnostically effective metal ion or metal-containing complex ion.

3. A compound of claim 1 which is metallated with at least one metal ion selected from the group consisting of radionuclides, paramagnetic ions, fluorescent ions, heavy metal ions or cluster ions.

4. A compound of claim 1 which is metallated with at least one metal ion selected from the group consisting of the metal ions of Ag, At, Au, Bi, Cu, Ga, Ho, In, Lu, Pb, Pd, Pm, Pr, Rb, Re, Rh, Sc, Sr, Tc, Tl, Y and Yb.

5. A compound of claim 3 wherein said radionuclide is selected from the group consisting of $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb and $^{141}$Ce.

6. A compound of claim 3, wherein said paramagnetic ion is selected from the group consisting of ions of transition and lanthanide metals having atomic numbers of 21–29, 42–44 and 57–71.

7. A compound of claim 1, which is coupled directly or indirectly to a vector moiety capable of targeting particular receptors, organs, tissues or body compartments.

8. A compound of claim 7 wherein said vector moiety is selected from the group consisting of proteins, antibodies, antibody fragments, oligopeptides, hormones, and polyalkylene oxides.

9. A pharmaceutical composition comprising an effective amount of a complex of a compound of claim 1 together with at least one pharmaceutically acceptable carrier or excipient.

10. A method of generating an image of an animated human or non-human animal subject involving administering a contrast agent to said subject and generating an image of at least a part of said subject to which said contrast agent has distributed, wherein said contrast agent is a complex of a compound of claim 1.

11. A method of treatment of cancer of an animate human or non-human animal subject involving administering a therapeutic agent to said subject, wherein said therapeutic agent is a complex of a compound of claim 1 with a therapeutically effective metal or metal-containing complex ion.

12. A process for the preparation of a complex of a compound of claim 1, said process comprising metallating a compound of claim 1 with a diagnostically or therapeutically effective metal ion or metal-containing complex ion.

13. A compound of claim 1 wherein R$^3$ is a thiol protecting group.

* * * * *

UNITED STATES PATENT AND TRADEMARK OFFICE
CERTIFICATE OF CORRECTION

PATENT NO. : 6,004,529

DATED : December 21, 1999

INVENTOR(S) : Shi-Bao Yu, et al.

It is certified that error appears in the above-identified patent and that said Letters Patent is hereby corrected as shown below:

Column 12, line 58, after "metal" insert --ion--.

Signed and Sealed this

Sixth Day of June, 2000

Q. TODD DICKINSON

*Attest:*

*Attesting Officer*        *Director of Patents and Trademarks*